United States Patent
Althorpe et al.

(10) Patent No.: US 10,195,373 B2
(45) Date of Patent: Feb. 5, 2019

(54) INHALER

(71) Applicants: INTERQUIM, S.A., Sant Cugat del Vallès (ES); LABORATORIOS CINFA, S.A., Huarte (ES)

(72) Inventors: Christopher John Althorpe, Cardiff (GB); Jonathan Paul Taylor, Stonehouse (GB)

(73) Assignees: INTERQUIM, S.A., Sant Cugat del Valles (ES); LABORATORIOS CINFA, S.A., Huarte (ES)

( * ) Notice: Subject to any disclaimer, the term of this patent is extended or adjusted under 35 U.S.C. 154(b) by 564 days.

(21) Appl. No.: 14/773,192

(22) PCT Filed: Mar. 8, 2013

(86) PCT No.: PCT/EP2013/054797
§ 371 (c)(1),
(2) Date: Sep. 4, 2015

(87) PCT Pub. No.: WO2014/135224
PCT Pub. Date: Sep. 12, 2014

(65) Prior Publication Data
US 2016/0022931 A1  Jan. 28, 2016

(51) Int. Cl.
*A61M 15/00* (2006.01)
*A61M 11/00* (2006.01)

(52) U.S. Cl.
CPC ...... *A61M 15/0025* (2014.02); *A61M 11/003* (2014.02); *A61M 15/003* (2014.02);
(Continued)

(58) Field of Classification Search
CPC .................. A61M 15/0025; A61M 15/0026
See application file for complete search history.

(56) References Cited

U.S. PATENT DOCUMENTS 6,135,771 A * 10/2000 Dragan .................. A61C 5/62
433/90
7,694,676 B2  4/2010 Wachtel
(Continued)

FOREIGN PATENT DOCUMENTS

WO  WO 2012/047182 A2  4/2012

OTHER PUBLICATIONS

International Search Report, dated Feb. 3, 2014, issued in PCT/EP2013/054797.
(Continued)

*Primary Examiner* — Nyca T Nguyen
(74) *Attorney, Agent, or Firm* — Birch, Stewart, Kolasch & Birch, LLP

(57) ABSTRACT

A dry powder inhaler comprises a shell having upper and lower shell parts, and an inhalation piece, through which a user can inhale medicament. The inhalation piece is coupled to the lower shell part and the upper shell part is moveable between a closed configuration, coupled to the lower shell part and covering the inhalation piece, and an open configuration in which the inhalation piece is exposed. An actuation button is coupled to the lower shell part and biased by a first biasing mechanism acting between the actuation button and the lower shell part towards a projected position projecting from the surface of the lower shell part and moveable to a retracted position. Movement of the actuation button causes medicament to be dispensed for subsequent inhalation through the inhalation piece.

20 Claims, 21 Drawing Sheets

(52) U.S. Cl.
CPC .... *A61M 15/0021* (2014.02); *A61M 15/0026* (2014.02); *A61M 15/0028* (2013.01); *A61M 15/0035* (2014.02); *A61M 15/0041* (2014.02); *A61M 2202/064* (2013.01); *A61M 2205/276* (2013.01); *A61M 2205/7545* (2013.01)

(56) References Cited

U.S. PATENT DOCUMENTS

| | | | |
|---|---|---|---|
| 8,377,009 B2* | 2/2013 | Sullivan | A61M 11/002 604/200 |
| 2008/0249473 A1* | 10/2008 | Rutti | A61M 5/158 604/157 |
| 2010/0300439 A1 | 12/2010 | Djupesland et al. | |
| 2010/0331765 A1* | 12/2010 | Sullivan | A61M 11/06 604/24 |

OTHER PUBLICATIONS

Written Opinion of the International Searching Authority, dated Feb. 3, 2014, issued in PCT/EP2013/054797.

\* cited by examiner

INHALER

TECHNICAL FIELD

The present disclosure relates to an inhaler, in particular, although not exclusively, to a dry powder inhaler.

BACKGROUND

Dry powder inhalers are widely used to dispense or release powdered medicament from a powder source which can then be inhaled by a patient. The powder source may be a capsule, a blister pack, a tape dose strip, an elongate peelable blister strip, a disk comprising several pre-metered doses or any other type of powder reservoir. One example of a dry powder inhaler includes U.S. Pat. No. 7,694,676.

Known single and multi-dose dry powder inhalers use either individual pre-measured doses, such as capsules, blisters or any other type of powder reservoirs, containing medicament which are inserted into the device prior to use, or incorporate a bulk powder reservoir, from which successive quantities of medicament are transferred to a dispensing chamber.

Dry powder inhalers typically comprise a housing, a mouthpiece or nosepiece, and a button for dispensing the medicament. In the case of capsule-based inhalers a medicament chamber is provided within which a powdered medicament capsule can be located and the button is provided with a piercing pin. In use, a capsule is located within the cavity and the button is depressed causing the pin to pierce the capsule and release the powdered medicament which can be inhaled into a user's respiratory tract through the mouthpiece. Similarly, in dry powder inhalers based on blisters or other pre-metered powder storage systems (any other type of powder reservoirs), by pressing a button, the blister or other pre-metered powder storage systems are pierced or otherwise opened, which allows the powder to be inhaled. In other dry powder inhalers, buttons are similarly used to trigger events that will end up with a medicament dose ready to be inhaled.

The present disclosure concerns developments and/or improvements relating to inhalers such as dry powder inhalers.

SUMMARY

According to a first aspect of the present disclosure there is provided a dry powder inhaler, comprising: a shell comprising an upper shell part and a lower shell part; an inhalation piece through which a user can inhale medicament, wherein the inhalation piece is coupled to the lower shell part and wherein the upper shell part is moveable between a closed configuration in which it is coupled to the lower shell part and covers the inhalation piece, and an open configuration in which the inhalation piece is exposed; an actuation button coupled to the lower shell part and biased by a first biasing device acting between the actuation button and the lower shell part towards a projected position in which it projects from the surface of the lower shell part and moveable to a retracted position; wherein in use, movement of the actuation button from the projected position towards the retracted position causes medicament to be dispensed for subsequent inhalation through the inhalation piece; and a latch which when engaged retains the actuation button in the retracted position.

In the retracted position, the actuation button may be substantially flush with the lower shell part. The latch may comprise a latching projection that can be located over a corresponding latching edge so as to engage the latch. The latching edge may be the edge of a latching recess within which the latching projection is located when located over the latching edge. The upper shell part may comprise the latching projection or the latching edge, and the actuation button may comprise the other of the latching projection or latching edge. When the actuation button is in the retracted position and the upper shell part is in the closed configuration, the latching projection may be located over the latching edge so as to engage the latch and retain the actuation button in the retracted position.

With the upper shell part in the closed configuration, movement of the actuation button from the projected position to the retracted position may cause the latching projection to locate over the latching edge and the latch to be engaged. The upper shell part may comprise the latching projection and the actuation button may comprise the latching edge and a ramp which is inclined and terminates towards the latching edge. With the upper shell part in the closed configuration, movement of the actuation button from the projected position to the retracted position may cause the latching projection to ride over the ramp, which may cause the upper shell part to resiliently move away from the closed configuration, allowing the latching projection to locate over the latching edge and the upper shell part to return to the closed configuration, thereby engaging the latch.

The upper shell part may be completely separable from the lower shell part. In other arrangements the upper shell part may be attached to the shell part such that are still moveable with respect to one another. For example, the upper shell part could be hinged to the lower shell part.

Regardless of the position of the actuation button, the first biasing device may apply a first spring force to the actuation button which acts in a direction towards the projected position. The inhaler may further comprise a second biasing device capable of acting between the actuation button and the lower shell part. Depending on the position of the actuation button, the second biasing device may apply a second spring force to the actuation button, the magnitude and the direction of action of which depends on the position of the actuation button. As the actuation button is moved towards the retracted position, the second spring force may act in a direction towards the projected position. When the actuation button is in the retracted position, the second spring force may act in a direction towards the retracted position. When the actuation button is in the projected position the second biasing device may not act on the actuation button. During initial movement of the actuation button from the retracted position towards the projected position caused by the first biasing device, the second spring force may act in a direction towards the retracted position so as to dampen the initial movement of the actuation button.

The second biasing device may comprise a ramp and a corresponding spring arm, the relative positions of which vary with the position of the actuation button. The magnitude and the direction of action of the second spring force may depend on the relative positions of the ramp and spring arm. The ramp may have first and second ramp surface portions inclined in generally opposing directions and which converge at a peak region. The lower shell part may comprise the ramp or spring arm, and the actuation button may comprise the other of the ramp or spring arm.

The inhaler may further comprise a medicament chamber in fluid communication with the inhalation piece and arranged to receive medicament, such as a sealed dose containing medicament. The sealed dose may be a capsule, a blister or any other type of powder reservoir. In use, movement of the actuation button from the projected position towards the retracted position may cause the medicament to be dispensed, for example from the sealed dose, such as by piercing, severing, or opening, so that it can subsequently be inhaled through the inhalation piece.

The inhaler may further comprise a piercing or opening element arranged such that in use movement of the actuation button from the projected position towards the retracted position causes a sealed dose, such as a capsule, located within the medicament chamber to be pierced or otherwise opened, thereby dispensing the medicament. The piercing or opening element may be attached to the actuation button.

A filter may be disposed between the medicament chamber and the inhalation piece so as to permit airflow from the medicament chamber to the inhalation piece, but retain the sealed dose, such as a capsule, or parts thereof within the medicament chamber.

The inhalation piece, the actuation button, and the medicament chamber may be part of a dispensing assembly. The dispensing assembly may be at least partially disposed within the lower shell part and may comprise a platform to which the medicament chamber is attached. The platform may extend across and may be attached to the lower shell part. The medicament chamber may be located within the lower shell part and the inhalation piece may be outside of the lower shell part. The platform may be detachably attached to the lower shell part such that the dispensing assembly can be detached and removed from the lower shell part. The upper shell part may be completely separable from the lower shell part and dispensing assembly. In other arrangements the upper shell part may be attached to the shell part such that are still moveable with respect to one another. For example, the upper shell part could be hinged to the lower shell part.

The inhaler may further comprise a locking arrangement configured such that during movement of the actuation button from the projected position towards the retracted position, the dispensing assembly is restricted from being removed from the lower shell part. The locking arrangement may be configured such that when the actuation button is in the retracted position, the dispensing assembly is restricted from being removed from the lower shell part. The locking arrangement may be configured such that the dispensing assembly can only be removed from the lower shell part when the actuation button is in the projected position. The locking arrangement may comprise a guide slot and a corresponding guide projection. The actuation button may comprise the guide slot or the guide projection, and the lower shell part may comprise the other of the guide slot and guide projection.

During movement of the actuation button from the projected position towards the retracted position, the guide projection may be located within the guide slot, thereby restricting the dispensing assembly from being removed from the lower shell part. Movement of the actuation button from the projected position towards the retracted position may cause the guide projection to slide in the guide slot. When the actuation button is in the retracted position, the guide projection may be located within the guide slot, thereby restricting the dispensing assembly from being removed from the lower shell part. When the actuation button is in the projected position, the guide projection may not be located within the guide slot, thereby permitting the dispensing assembly to be removed from the lower shell part.

The inhalation piece may be moveable with respect to the platform between a normal inhaling position and a loading position in which the medicament chamber is exposed such that a sealed dose, such as a capsule or blister or any other type of powder reservoir, can be received therein. In the inhaling position the inhalation piece may be in fluid communication with and may cover the medicament chamber so as to prevent a sealed dose received therein from being removed. The filter may be attached to the inhalation piece and may be disposed between the medicament chamber and the inhalation piece only when the inhalation piece is in the inhaling position.

The inhalation piece may be hingedly coupled to the platform by a hinge such that it is pivotably moveable between the inhaling position and the loading position. The hinge may be a separable hinge having first and second hinge parts, one of which is attached to the inhalation piece and the other of which is attached to the platform. The first and second hinge parts may be separated so as to separate the inhalation piece and platform. The force required to separate the first and second hinge parts may be less than the force required to structurally damage either the first or second hinge part. The first hinge part may comprise a rod and the second hinge part may comprise a corresponding slotted opening within which the rod is removably disposed such that it can rotate within the opening and such that the rod and opening are separable. The slotted opening may be an elongate slotted channel.

According to a second aspect of the present disclosure there is provided a dry powder inhaler, comprising: a shell comprising an upper shell part and a lower shell part which are completely separable; an inhalation piece through which a user can inhale medicament, wherein the inhalation piece is coupled to the lower shell part and wherein the upper shell part is moveable between a closed configuration in which it is coupled to the lower shell part and covers the inhalation piece, and an open configuration in which the inhalation piece is exposed; and an actuation button; wherein in use, movement of the actuation button causes medicament to be dispensed for subsequent inhalation through the inhalation piece; wherein the upper shell part is provided with at least one orienting formation such that the upper shell part can be coupled to the lower shell part in the closed configuration only in a single correct orientation.

The orienting formation may comprise a projection that locates within a corresponding recess when the upper shell part is coupled to the lower shell part in the closed configuration in the correct orientation.

According to a third aspect of the present disclosure there is provided a dry powder inhaler, comprising: a shell comprising a lower shell part; an inhalation piece coupled to the lower shell part and through which a user can inhale medicament; an actuation button coupled to the lower shell part and biased by a first biasing device acting between the actuation button and the lower shell part towards a projected position in which it projects from the surface of the lower shell part and moveable to a retracted position; wherein in use, movement of the actuation button from the projected position towards the retracted position causes medicament to be dispensed for subsequent inhalation through the inhalation piece; and a second biasing device capable of acting between the actuation button and the lower shell part, wherein depending on the position of the actuation button, the second biasing device applies a second spring force to the actuation button, the magnitude and the direction of action of which depends on the position of the actuation button.

Regardless of the position of the actuation button, the first biasing device may apply a first spring force to the actuation button which acts in a direction towards the projected position. As the actuation button is moved towards the retracted position, the second spring force may act in a direction towards the projected position. When the actuation button is in the retracted position, the second spring force may act in a direction towards the retracted position. When the actuation button is in the projected position the second biasing device may not act on the actuation button. During initial movement of the actuation button from the retracted position towards the projected position caused by the first biasing device, the second spring force may act in a direction towards the retracted position so as to dampen the initial movement of the actuation button.

The second biasing device may comprise a ramp and a corresponding spring arm, the relative positions of which vary with the position of the actuation button. The magnitude and the direction of action of the second spring force may depend on the relative positions of the ramp and spring arm. The ramp may have first and second ramp surface portions inclined in generally opposing directions and which converge at a peak region. When the actuation button is in the projected position, the ramp and spring arm may not be in contact. The lower shell part may comprise the ramp or spring arm, and the actuation button may comprise the other of the ramp or spring arm. The lower shell part may comprise the ramp and the actuation button may comprise the spring arm.

According to a fourth aspect of the present disclosure there is provided dry powder inhaler, comprising: an inhalation piece through which a user can inhale medicament; an actuation button; and a medicament chamber in fluid communication with the inhalation piece and arranged to receive medicament, for example a sealed dose, such as a capsule, blister or other type of powder reservoir, containing medicament, wherein in use, movement of the actuation button causes the medicament to be dispensed, for example from the sealed dose, such as by piercing, severing, or opening, so that it can subsequently be inhaled through the inhalation piece; and a filter moulded from a plastics material disposed between the medicament chamber and the inhalation piece so as to permit airflow from the medicament chamber to the inhalation piece, but retain the sealed dose or parts thereof within the medicament chamber.

The inhaler may further comprise a piercing or opening element arranged such that in use movement of the actuation button from the projected position towards the retracted position causes a sealed dose, such as a capsule, located within the medicament chamber to be pierced or otherwise opened, thereby dispensing the medicament. The piercing or opening element may be attached to the actuation button. The filter may be moulded from one or more plastics material selected from the group consisting of: ABS (Acrylonitrile Butadiene Acrylate), PC (Polycarbonate), PC/ABS (blend of ABS & PC), PP (Polypropylene), PS (Polystyrene), MABS (methyl methacrylate-acrylonitrile-butadiene-styrene), AMMA Poly (Acrylonitrile Methyl Methacrylate), PA (Polyamide also known as Nylon) and PBT (Polybutylene Terephthalate).

According to a fifth aspect of the present disclosure there is provided a dry powder inhaler, comprising: a shell comprising an upper shell part and a lower shell part which are completely separable; and a dispensing assembly at least partially disposed within the lower shell part and comprising a platform extending across and attached to the lower shell part, the dispensing assembly comprising: an inhalation piece through which a user can inhale medicament; an actuation button; and a medicament chamber, attached to the platform, in fluid communication with the inhalation piece and arranged to receive medicament, for example a sealed dose, such as a capsule, blister, or any other type of powder reservoir, containing medicament, wherein in use, movement of the actuation button causes the medicament to be dispensed, for example from the sealed dose, such as by piercing, severing, or opening, so that it can subsequently be inhaled through the inhalation piece; wherein the upper shell part is moveable between a closed configuration in which it is coupled to the lower shell part and covers the inhalation piece, and an open configuration in which the inhalation piece is exposed; and wherein the upper shell part and the platform are provided with corresponding retention formations which can be engaged so as to releasably retain the upper shell part in the closed configuration.

The medicament chamber may be located within the lower shell part and the inhalation piece may be outside of the lower shell part. The platform may be detachably attached to the lower shell part such that the dispensing assembly can be detached and removed from the lower shell part. The platform and the lower shell part may be provided with corresponding fixing formations which are engaged so as to detachably attach the platform to the lower shell part. The fixing formations may comprise at least one fixing projection and at least one corresponding fixing recess.

According to a sixth aspect of the present disclosure there is provided a dry powder inhaler, comprising: a shell comprising a lower shell part; a dispensing assembly at least partially disposed within the lower shell part and comprising a platform extending across and detachably attached to the lower shell part such that the dispensing assembly can be detached and removed from the lower shell part, the dispensing assembly comprising: an inhalation piece through which a user can inhale medicament; an actuation button; and a medicament chamber, attached to the platform, in fluid communication with the inhalation piece and arranged to receive medicament, for example a sealed dose, such as a capsule, blister, or any other type of powder reservoir, containing medicament, wherein in use, movement of the actuation button causes the medicament to be dispensed, for example from the sealed dose, such as by piercing, severing, or opening, so that it can subsequently be inhaled through the inhalation piece; and a locking arrangement configured such that during movement of the actuation button from the projected position towards the retracted position, the dispensing assembly is restricted from being removed from the lower shell part.

The locking arrangement may be configured such that when the actuation button is in the retracted position, the dispensing assembly is restricted from being removed from the lower shell part. The locking arrangement may be configured such that the dispensing assembly can only be removed from the lower shell part when the actuation button is in the projected position. The locking arrangement may comprise a guide slot and a corresponding guide projection. The actuation button may comprise the guide slot or the guide projection, and the lower shell part comprises the other of the guide slot and guide projection. The actuation button may comprise the guide slot and the lower shell part may comprise the guide projection.

During movement of the actuation button from the projected position towards the retracted position, the guide projection may be located within the guide slot, thereby restricting the dispensing assembly from being removed from the lower shell part. Movement of the actuation button from the projected position towards the retracted position may cause the guide projection to slide in the guide slot. When the actuation button is in the retracted position, the guide projection may be located within the guide slot, thereby restricting the dispensing assembly from being removed from the lower shell part. When the actuation button is in the projected position, the guide projection may not be located within the guide slot, thereby permitting the dispensing assembly to be removed from the lower shell part. There may be a plurality of guide slots and a plurality of guide projections.

According to a seventh aspect of the present disclosure there is provided a dry powder inhaler, comprising: a dispensing assembly comprising: a platform; an inhalation piece through which a user can inhale medicament; an actuation button; and a medicament chamber, attached to the platform, in fluid communication with the inhalation piece and arranged to receive medicament, for example a sealed dose, such as a capsule, blister, or any other type of powder reservoir, containing medicament, wherein in use, movement of the actuation button causes the medicament to be dispensed, for example from the sealed dose, such as by piercing, severing, or opening, so that it can subsequently be inhaled through the inhalation piece: wherein the inhalation piece is moveable with respect to the platform between a normal inhaling position and a loading position in which the medicament chamber is exposed such that a sealed dose can be received therein, wherein in the inhaling position the inhalation piece is in fluid communication with and covers the medicament chamber so as to prevent a sealed dose received therein from being removed; wherein the inhalation piece is provided with two coupling formations provided on opposing sides thereof, and wherein the platform is provided with two corresponding coupling formations which are engaged so as to releasably retain the inhalation piece in the inhaling position; and wherein grips are provided on opposing sides of the inhalation piece which can be gripped by a user's fingers so as to resiliently deform the inhalation piece, thereby disengaging the coupling formations and allowing the inhalation piece to be moved from the inhaling position to the loading position.

A filter may be disposed between the medicament chamber and the inhalation piece so as to permit airflow from the medicament chamber to the inhalation piece, but retain the sealed dose, such as a capsule, blister, or any other type of powder reservoir, or parts thereof within the medicament chamber. The filter may be attached to the inhalation piece and may be disposed between the medicament chamber and the inhalation piece only when the inhalation piece is in the inhaling position.

The coupling formations may comprise at least one coupling projection and at least one corresponding coupling recess. The inhalation piece may be hingedly coupled to the platform by a hinge such that it is pivotably moveable between the inhaling position and the loading position.

The hinge may be a separable hinge having first and second hinge parts, one of which is attached to the inhalation piece and the other of which is attached to the platform. The first and second hinge parts may be separated so as to separate the inhalation piece and platform. The first hinge part may be attached to the inhalation piece and the second hinge part may be attached to the platform. The force required to separate the first and second hinge parts may be less than the force required to structurally damage either the first or second hinge part. The first hinge part may comprise a rod and the second hinge part may comprise a corresponding slotted opening within which the rod is removably disposed such that it can rotate within the opening and such that the rod and opening are separable. The slotted opening may be an elongate slotted channel.

The inhalation piece may be a mouthpiece or a nosepiece.

According to a broad aspect of the present disclosure there is provided an inhaler, comprising: a shell comprising an upper shell part and a lower shell part; an inhalation piece through which a user can inhale medicament, wherein the inhalation piece is coupled to the lower shell part and wherein the upper shell part is moveable between a closed configuration in which it is coupled to the lower shell part and covers the inhalation piece, and an open configuration in which the inhalation piece is exposed; and an actuation button coupled to the lower shell part and biased by a first biasing device acting between the actuation button and the lower shell part towards a projected position in which it projects from the surface of the lower shell part and moveable to a retracted position; wherein in use, movement of the actuation button from the projected position towards the retracted position causes medicament to be dispensed for subsequent inhalation through the inhalation piece.

The inhaler may further comprise a latch which when engaged retains the actuation button in the retracted position. In the retracted position, the actuation button may be substantially flush with the lower shell part.

The latch may comprise a latching projection that can be located over a corresponding latching edge so as to engage the latch. The latching edge may be the edge of a latching recess within which the latching projection is located when located over the latching edge. The upper shell part may comprise the latching projection or the latching edge, and the actuation button may comprise the other of the latching projection or latching edge. When the actuation button is in the retracted position and the upper shell part is in the closed configuration, the latching projection may be located over the latching edge so as to engage the latch and retain the actuation button in the retracted position. With the upper shell part in the closed configuration, movement of the actuation button from the projected position to the retracted position may cause the latching projection to locate over the latching edge and the latch to be engaged. The upper shell part may comprise the latching projection and the actuation button may comprise the latching edge and a ramp which is inclined and terminates towards the latching edge. With the upper shell part in the closed configuration, movement of the actuation button from the projected position to the retracted position may cause the latching projection to ride over the ramp, which may cause the upper shell part to resiliently move away from the closed configuration, allowing the latching projection to locate over the latching edge and the upper shell part to return to the closed configuration, thereby engaging the latch.

The upper shell part may be completely separable from the lower shell part. The upper shell part may be provided with at least one orienting formation such that the upper shell part can be coupled to the lower shell part in the closed configuration only in a single correct orientation. The orienting formation may comprise a projection that locates within a corresponding recess when the upper shell part is coupled to the lower shell part in the closed configuration in the correct orientation.

Regardless of the position of the actuation button, the first biasing device may apply a first spring force to the actuation button which acts in a direction towards the projected position.

The inhaler may further comprise a second biasing device capable of acting between the actuation button and the lower shell part. Depending on the position of the actuation button, the second biasing device may apply a second spring force to the actuation button. The magnitude and the direction of action of the second spring force may depend on the position of the actuation button. As the actuation button is moved towards the retracted position, the second spring force may act in a direction towards the projected position. When the actuation button is in the retracted position, the second spring force may act in a direction towards the retracted position. When the actuation button is in the projected position the second biasing device may not act on the actuation button. During initial movement of the actuation button from the retracted position towards the projected position caused by the first biasing device, the second spring force may act in a direction towards the retracted position so as to dampen the initial movement of the actuation button.

The second biasing device may comprise a ramp and a corresponding spring arm, the relative positions of which vary with the position of the actuation button. The magnitude and the direction of action of the second spring force may depend on the relative positions of the ramp and spring arm. The ramp may have first and second ramp surface portions inclined in generally opposing directions and which converge at a peak region. When the actuation button is in the projected position, the ramp and spring arm may not be in contact. The lower shell part may comprise the ramp or spring arm, and the actuation button may comprise the other of the ramp or spring arm. The lower shell part may comprise the ramp and the actuation button may comprise the spring arm.

The inhaler may further comprise a medicament chamber in fluid communication with the inhalation piece and arranged to receive medicament, for example a sealed dose, such as a capsule, blister, or any other type of powder reservoir, containing medicament. In use, movement of the actuation button from the projected position towards the retracted position may cause the medicament to be dispensed, for example from the sealed dose, such as by piercing, severing, or opening, so that it can subsequently be inhaled through the inhalation piece.

The inhaler may further comprise a piercing or opening element arranged such that in use movement of the actuation button from the projected position towards the retracted position causes a sealed dose located within the medicament chamber to be pierced or otherwise opened, thereby dispensing the medicament. The piercing or opening element may be attached to the actuation button.

A filter may be disposed between the medicament chamber and the inhalation piece so as to permit airflow from the medicament chamber to the inhalation piece, but retain the sealed dose or parts thereof within the medicament chamber. The filter may be moulded from a plastics material. The filter may be moulded from one or more plastics material selected from the group consisting of: ABS (Acrylonitrile Butadiene Acrylate), PC (Polycarbonate), PC/ABS (blend of ABS & PC), PP (Polypropylene), PS (Polystyrene), MABS (methyl methacrylate-acrylonitrile-butadiene-styrene), AMMA Poly (Acrylonitrile Methyl Methacrylate), PA (Polyamide also known as Nylon) and PBT (Polybutylene Terephthalate).

The inhalation piece, the actuation button, and the medicament chamber may be part of a dispensing assembly, the dispensing assembly at least partially disposed within the lower shell part and comprising a platform to which the medicament chamber is attached. The platform may extend across and may be attached to the lower shell part. The medicament chamber may be located within the lower shell part and the inhalation piece may be outside of the lower shell part. The platform may be detachably attached to the lower shell part such that the dispensing assembly can be detached and removed from the lower shell part.

The platform and the lower shell part may be provided with corresponding fixing formations which are engaged so as to detachably attach the platform to the lower shell part. The fixing formations may comprise at least one fixing projection and at least one corresponding fixing recess.

The upper shell part may be completely separable from the lower shell part and dispensing assembly. The upper shell part and the platform may be provided with corresponding retention formations which can be engaged so as to releasably retain the upper shell part in the closed configuration.

The inhaler may further comprise a locking arrangement configured such that during movement of the actuation button from the projected position towards the retracted position, the dispensing assembly is restricted from being removed from the lower shell part. The locking arrangement may be configured such that when the actuation button is in the retracted position, the dispensing assembly is restricted from being removed from the lower shell part. The locking arrangement may be configured such that the dispensing assembly can only be removed from the lower shell part when the actuation button is in the projected position. The locking arrangement may comprise a guide slot and a corresponding guide projection. The actuation button may comprise the guide slot or the guide projection, and the lower shell part may comprise the other of the guide slot and guide projection. The actuation button may comprise the guide slot and the lower shell part may comprise the guide projection.

During movement of the actuation button from the projected position towards the retracted position, the guide projection may be located within the guide slot, thereby restricting the dispensing assembly from being removed from the lower shell part. Movement of the actuation button from the projected position towards the retracted position may cause the guide projection to slide in the guide slot. When the actuation button is in the retracted position, the guide projection may be located within the guide slot, thereby restricting the dispensing assembly from being removed from the lower shell part. When the actuation button is in the projected position, the guide projection may not be located within the guide slot, thereby permitting the dispensing assembly to be removed from the lower shell part. There may be a plurality of guide slots and a plurality of guide projections.

The inhalation piece may be moveable with respect to the platform between a normal inhaling position and a loading position in which the medicament chamber is exposed such that a sealed dose can be received therein. In the inhaling position the inhalation piece may be in fluid communication with and cover the medicament chamber so as to prevent a sealed dose received therein from being removed. The or a filter may be attached to the inhalation piece and may be disposed between the medicament chamber and the inhalation piece only when the inhalation piece is in the inhaling position.

The inhalation piece and platform may be provided with corresponding coupling formations which are engaged so as to releasably retain the inhalation piece in the inhaling position. The coupling formations may comprise at least one coupling projection and at least one corresponding coupling recess. The coupling formations may comprise two coupling formations provided on the inhalation piece and a two corresponding coupling formations provided on the platform. Coupling formations may be provided on opposing sides of the inhalation piece. Grips may be provided on opposing sides of the inhalation piece which can be gripped by a user's fingers so as to resiliently deform the inhalation piece, thereby disengaging the coupling formations and allowing the inhalation piece to be moved from the inhaling position to the loading position.

The inhalation piece may be hingedly coupled to the platform by a hinge such that it is pivotably moveable between the inhaling position and the loading position. The hinge may be a separable hinge having first and second hinge parts, one of which is attached to the inhalation piece and the other of which is attached to the platform. The first and second hinge parts may be be separated so as to separate the inhalation piece and platform. The first hinge part may be attached to the inhalation piece and the second hinge part may be attached to the platform. The force required to separate the first and second hinge parts may be less than the force required to structurally damage either the first or second hinge part. The first hinge part may comprise a rod and the second hinge part may comprise a corresponding slotted opening within which the rod is removably disposed such that it can rotate within the opening and such that the rod and opening are separable. The slotted opening may be an elongate slotted channel.

The inhalation piece may be a mouthpiece or a nosepiece.

The inhaler may be a dry powder inhaler.

The present inhaler may comprise any combination of the features and/or limitations referred to herein, except combinations of such features as are mutually exclusive.

BRIEF DESCRIPTION OF THE DRAWINGS

Examples of the inhaler will now be described with reference to the accompanying drawings, in which.

DETAILED DESCRIPTION

Figure 1:
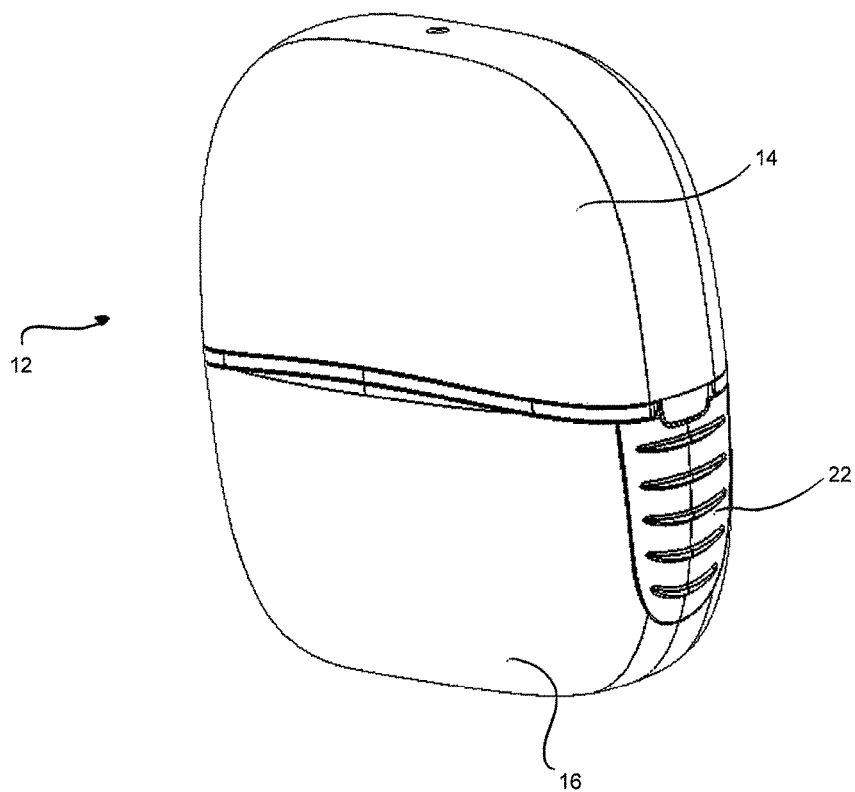
FIG. 1 schematically shows a perspective view of a dry powder inhaler according to one example of the inhaler.
Figure 2:
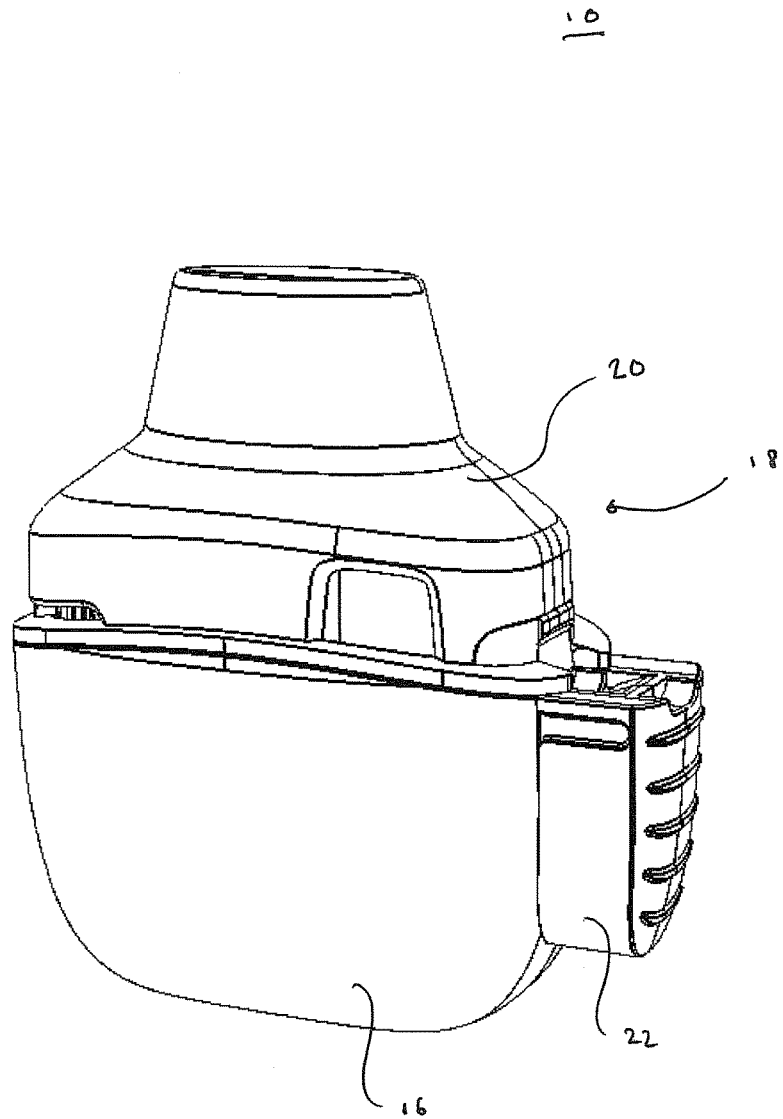
FIG. 2 schematically shows the inhaler of FIG. 1 with the upper shell part removed.

FIGS. 1 and 2 show a dry powder inhaler 10 comprising a shell 12 having an upper shell part 14 and a lower shell part 16. As will be described in detail below, a dispensing assembly 18 is removably located in the lower shell part 16 and comprises an inhalation piece in the form of a mouthpiece 20 which projects from the lower shell part 16. The upper shell part 14 can be indirectly attached to the lower shell part 16 in a closed configuration so as to cover the mouthpiece 20 (FIG. 1), and can be completely removed to an open configuration so as to expose the mouthpiece 20. The dispensing assembly 18 also comprises a medicament chamber, such as a capsule chamber, (not shown) and an actuation button 22 which is shown in FIG. 1 in a retracted position in which it is substantially flush with the outer surface of the lower shell part 16, and in FIG. 2 in a projected position in which it projects from the outer surface of the lower shell part 16. In use, a sealed dose of medicament, such as a dry powder capsule of medicament, a blister of medicament, or any other type of powder reservoir, can be received within the medicament chamber and movement of the actuation button 22 causes the capsule to be pierced or otherwise opened and the medicament to be released (or dispensed). The released dry powder medicament can then be inhaled by a patient through the mouthpiece 20.

Figure 3:
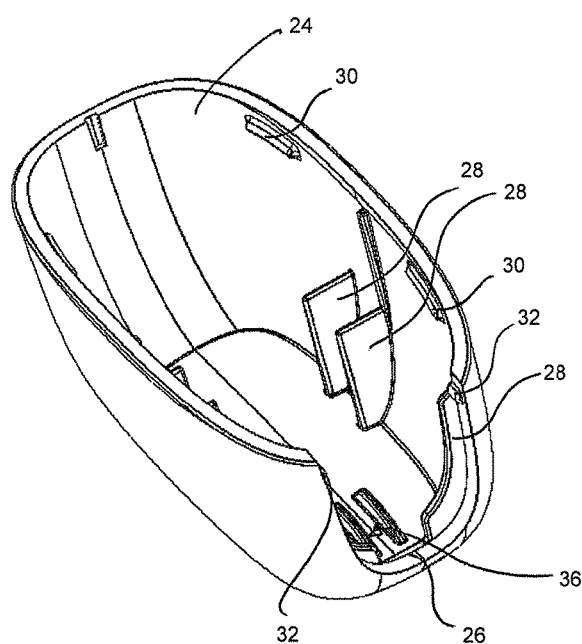
FIG. 3 schematically shows a perspective view of the lower shell part.
Figure 4:
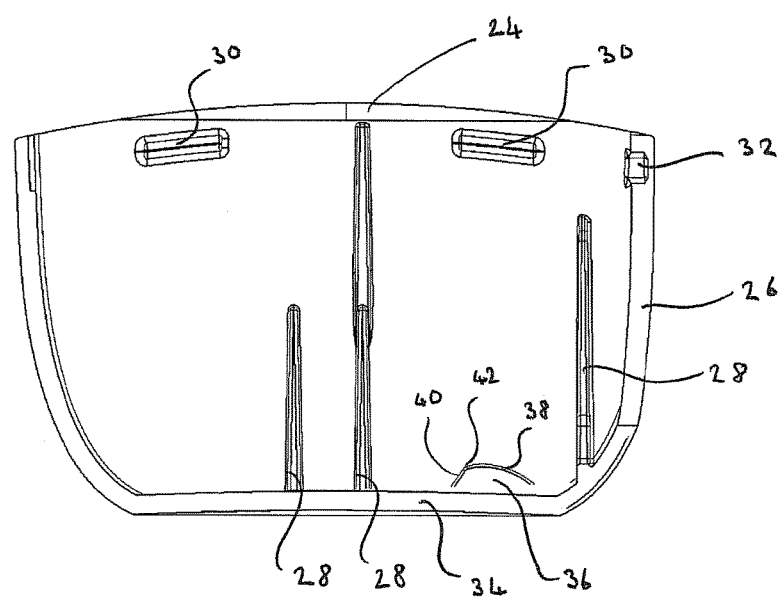
FIG. 4 schematically shows a cross-sectional view of the lower shell part.

Referring to FIGS. 3 and 4, the lower shell part 16 is integrally formed from a plastics material by an injection moulding process and includes a number of integrally formed features. The lower shell part 16 is substantially hollow and comprises an open top 24 and a button cut-out 26 on one side. A number of ribs 28 are formed on the inside of the lower shell part 16 and act to stiffen the lower shell part 16 and help to locate the dispensing assembly 18. Two retaining formations in the form of retaining projections 30 are formed on either side of the inner surface of the lower shell part 16 towards the open top 24 and, as will be described below, these cooperate with the dispensing assembly 18 so as to retain the dispensing assembly within the lower shell part 16. Each side of the button cut-out 26 is provided with a guide projection 32 that slightly projects into the button cut-out 26. The guide projections 32 cooperate with the actuation button 22 as will be described below. The base 34 of the lower shell part 16 is provided with a spring ramp 36 that is adjacent to the button cut-out 26 and which comprises first and second ramp surfaces 38, 40 which are inclined in opposing directions and which converge at a peak region 42. The first ramp surface 38 is inclined in a direction away from the button cut-out 26 and the second ramp surface 40 is inclined in a direction towards the button cut-out. Whilst the second ramp surface 40 is of a constant gradient, the first ramp surface 38 has a curved profile and the gradient decreases in a direction away from the button cut-out 26. The spring ramp 36 is configured to cooperate with a spring arm provided on the actuation button 22 as will be described in detail below.

Figure 5:
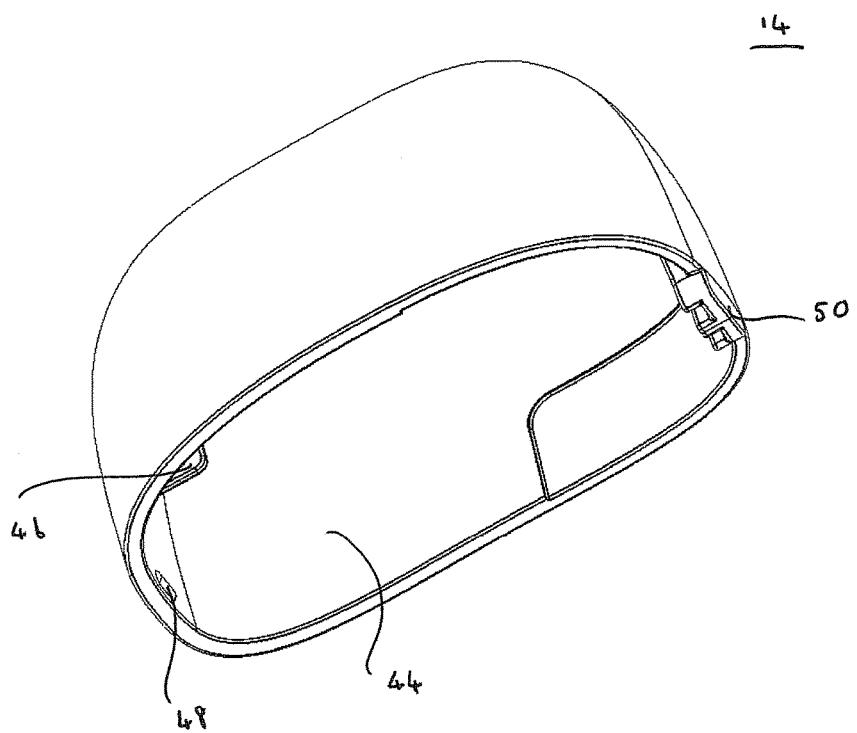
FIG. 5 schematically shows a perspective view of the upper shell part.
Figure 6:
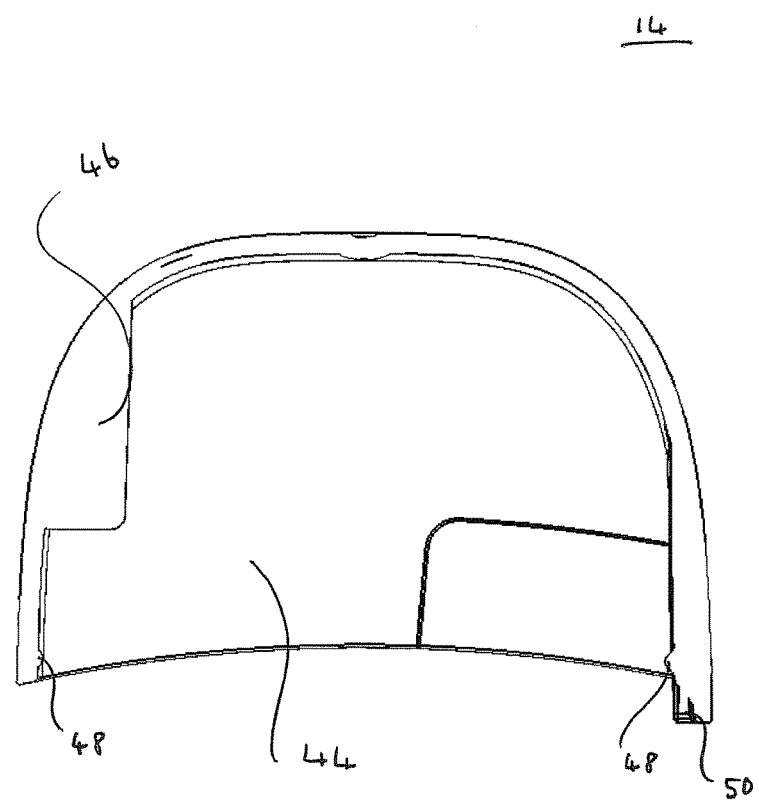
FIG. 6 schematically shows a cross-sectional view of the upper shell part.

Referring now to FIGS. 5 and 6, the upper shell part 14, like the lower shell part 16, is integrally formed from a plastics material by an injection moulding process and includes a number of integrally formed features. The upper shell part 14 is substantially hollow and comprises an open bottom 44. A rib 46 is formed on the inside of the upper shell part 14 and acts to stiffen it and helps to locate it over the mouthpiece 20. A retention formation in the form of a retention projection 48 are formed on either end of the inner surface of the upper shell part 14 towards the open bottom 44. As will be described below, these cooperate with the dispensing assembly 18 to releasably retain the upper shell part 14 in the closed configuration. The upper shell part 14 also comprises a latching projection 50 that downwardly extends from a side of the upper shell part 14. The latching projection 50 cooperates with the actuation button 22 to retain it in a retracted, or stowed, position. This will be described in detail below.

Figure 7:
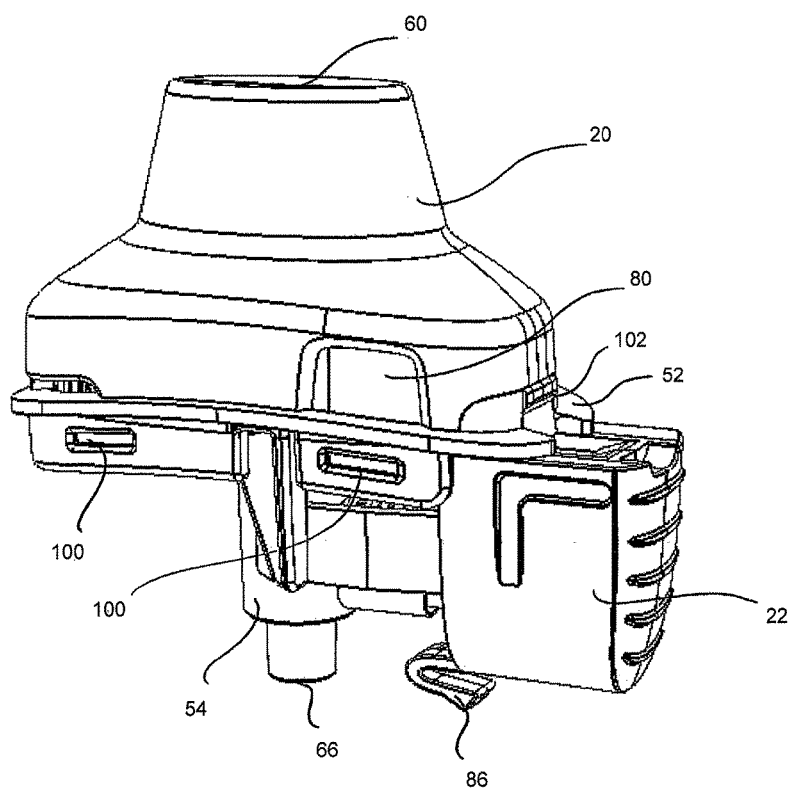
FIG. 7 schematically shows a perspective view of the dispensing assembly.
Figure 8:
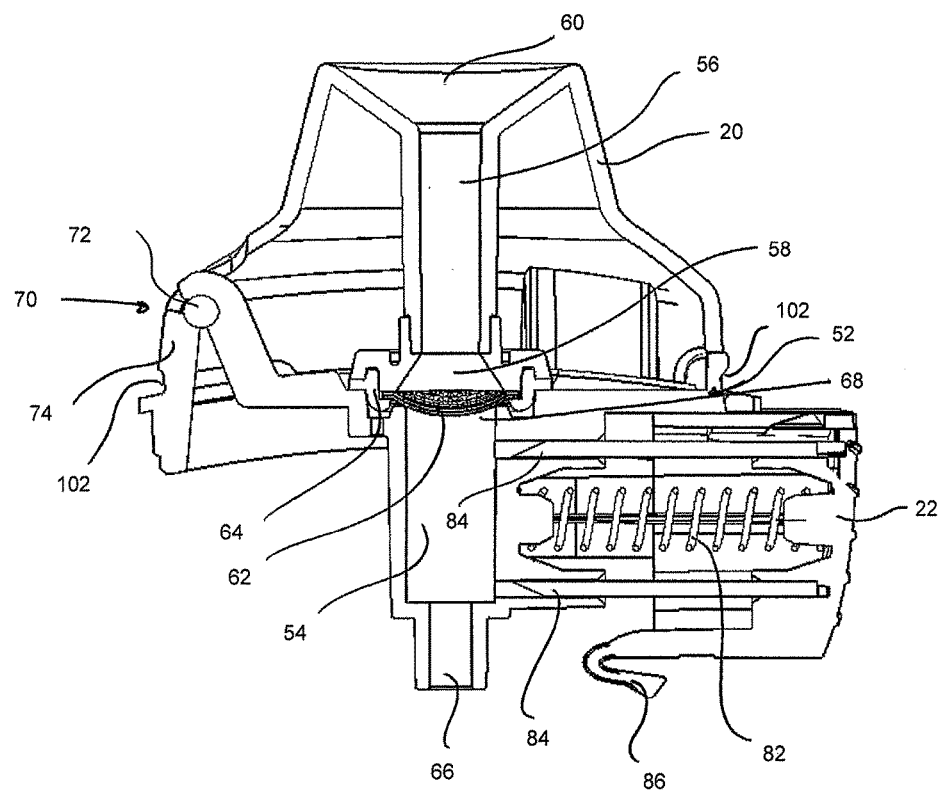
FIG. 8 schematically shows a cross-sectional view of the dispensing assembly.

FIGS. 7 and 8 show the dispensing assembly 18 which is a multipart assembly comprising a number of different components. The dispensing assembly 18 comprises the mouthpiece 20, the actuation button 22, a platform member 52, and a capsule or medicament chamber 54. The mouthpiece 20 is moulded from a plastics material and includes an inhalation passageway 56 extending through the mouthpiece 20 having an inlet 58 towards the bottom and outlet 60 towards the top. A filter 62 is provided at the inlet 58 of the inhalation passageway 56 of the mouthpiece 20 and is retained in place with a fitting 64. In this particular example the filter 62 is a metal mesh filter. However, in some examples the filter 62 may be an injection moulded component manufactured from a plastics material ABS (Acrylonitrile Butadiene Acrylate), PC (Polycarbonate), PC/ABS (blend of ABS & PC), PP (Polypropylene), PS (Polystyrene), MABS (methyl methacrylate-acrylonitrile-butadiene-styrene), AMMA Poly (Acrylonitrile Methyl Methacrylate), PA (Polyamide also known as Nylon) and PBT (Polybutylene Terephthalate). The platform member 52 and medicament chamber 54 are integrally formed from a plastics material. The medicament chamber 54 is substantially cylindrical and comprises a small diameter inlet 66 and a larger diameter outlet 68 that terminates at and extends through the platform member 52.

The mouthpiece 20 is hingedly connected to the platform member 52 by a hinge 70 having a first hinge part 72 which is part of the mouthpiece 20 and a second hinge part 74 which is part of the platform member 52. In this example the first hinge part is a rod 72 and the second hinge part is an elongate slotted channel 74. The construction of the elongate slotted channel 74 allows the rod 72 to be snap-fitted within it so that it can rotate about a longitudinal axis. As will be described below, the rod 72 can be removed from the channel 74 so as to separate the mouthpiece 20 from the platform member 52.

Figure 9:
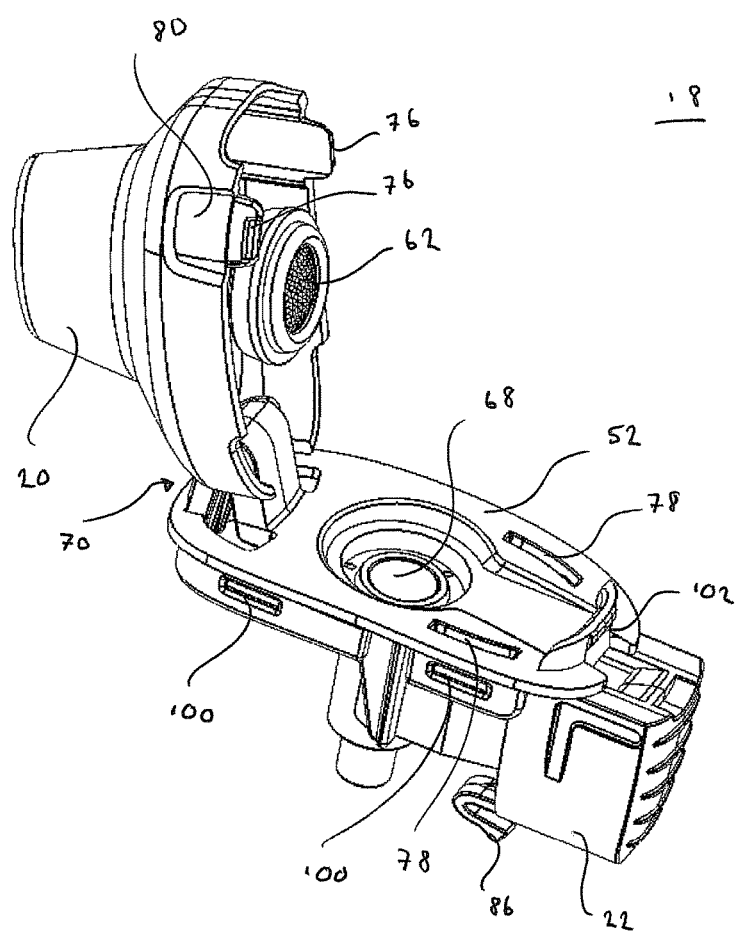
FIG. 9 schematically shows a perspective view of the dispensing assembly with the mouthpiece in the loading position.

The hinge 70 allows the mouthpiece 20 to be pivoted with respect to the platform member 52 between an inhaling position (FIG. 7) and a loading position (FIG. 9). In the inhaling position, the inlet 58 of the inhalation passageway 56 of the mouthpiece 20 is adjacent to the outlet 68 of the medicament chamber 54 with the filter 62 disposed between the inhalation passageway 56 and the medicament chamber 54. In the loading position, the mouthpiece 20 is pivoted away from the platform member 52 and the outlet 68 of the medicament chamber 54 is exposed so that a sealed dose, such as a medicament capsule, can be loaded into the medicament chamber 54.

Each side of the mouthpiece 20 is provided with a coupling formation in the form of a coupling projection 76. Similarly, each side of the platform member 52 is provided with a corresponding coupling formation in the form of a coupling recess 78. The side regions of the mouthpiece 20 in the region of the coupling projections 76 are of a reduced thickness and provide grips 80. In the inhaling position (FIG. 7), the coupling projections 76 are engaged with the coupling recesses 78 so as to prevent the mouthpiece 20 from moving away from the inhaling position. In order to allow the mouthpiece 20 to be pivoted to the loading position, a user can pinch the opposing grips 80 between a thumb and forefinger which causes the mouthpiece 20 to slightly resiliently deform, thereby disengaging the coupling projections and recesses 76, 78.

Figure 10:
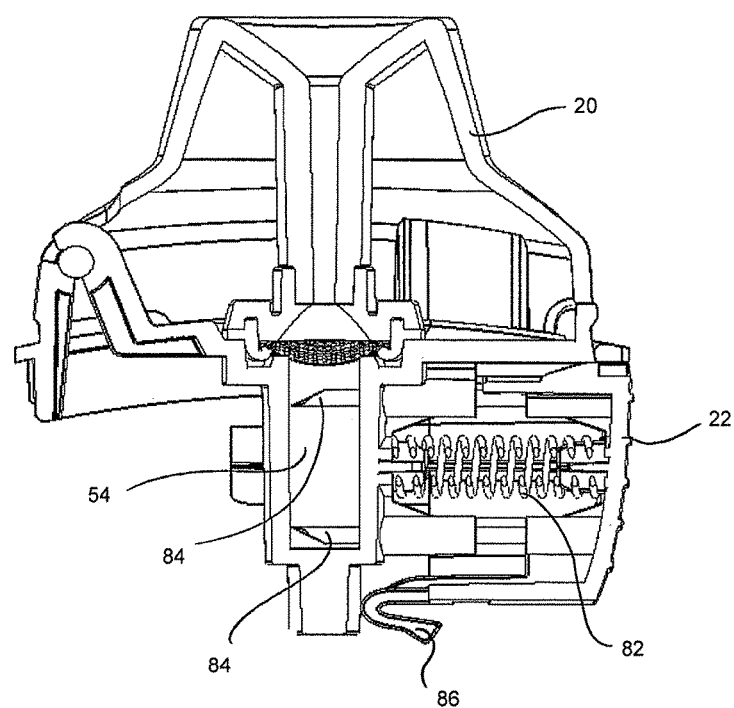
FIG. 10 schematically shows a cross-sectional view of the dispensing assembly with the actuation button in the retracted position.

The actuation button 22 is integrally formed from a plastics material and is slidable with respect to the platform member 52 and medicament chamber 54. The actuation button 22 is biased with a first biasing device in the form of a metal coil spring 82 to a projected position (FIGS. 7 and 8) and is moveable to a retracted position (FIG. 10). Two piercing (or opening) elements 84 in the form of needles are attached to the actuation button 22 and in the projected position are outside of the medicament chamber 54 and enter the medicament chamber 54 upon movement to the retracted position. The bottom surface of the actuation button 22 is provided with a resilient spring arm 86 in the form of the hook which, as will be described in detail below, cooperates with the spring ramp 36 of the lower shell part 16 to provide a second biasing device.

Figure 11:
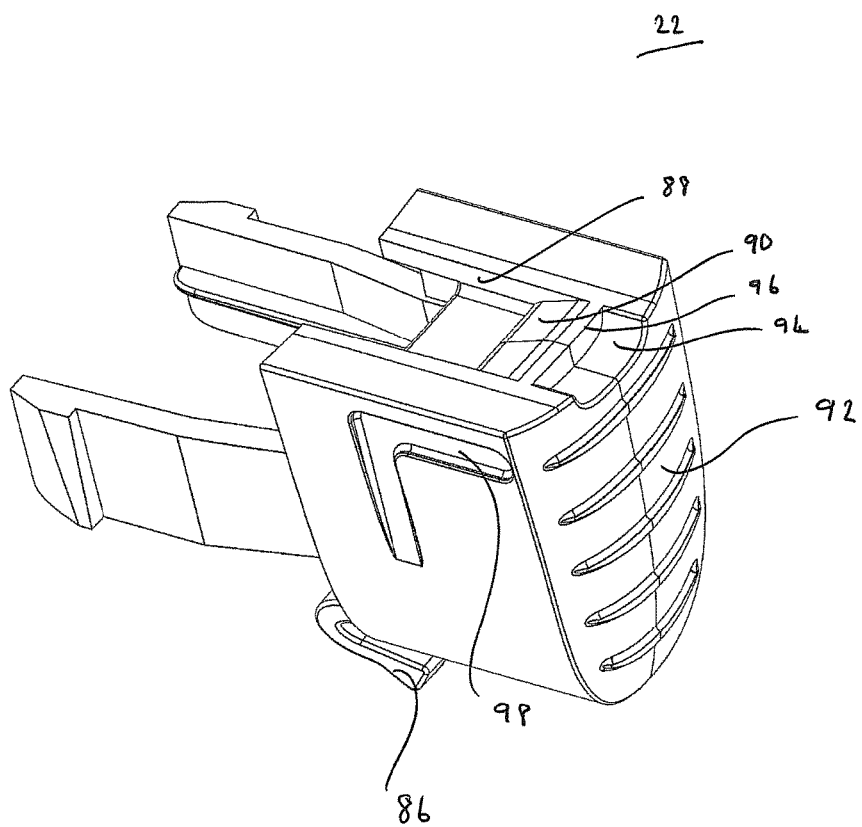
FIG. 11 schematically shows a perspective view of the actuation button.

As best shown in FIG. 11, the upper surface of the actuation button 22 comprises a channel 88 within which is provided a ramp 90 that is inclined in a direction towards the front surface 92 of the actuation button 22. Beyond the ramp 90, a latching recess 94 is provided that comprises a latching edge 96. The shape of the latching recess 94 corresponds to that of the latching projection 50 of the upper shell part 14 and they cooperate to provide a latch. Each side of the actuation button 22 is provided with a longitudinally extending guide slot 98 that, as will be described below, cooperates with a corresponding guide projection 32 provided by the lower shell part 16.

Referring back to FIGS. 7 and 9, each side of the platform member 52 is provided with two retaining formations in the form of retaining recesses 100 that are arranged to cooperate with the retaining projections 30 of the lower shell part 16 so as to retain the dispensing assembly 18 within the lower shell part 16. As shown in FIGS. 7 and 8, each end of the platform member 52 is provided with a retention formation in the form of a retention recess 102 that is arranged to cooperate with a corresponding retention projection 48 formed on the inner surface of the upper shell part 14 so as to retain the upper shell part 14 in the closed configuration.

Figure 12:
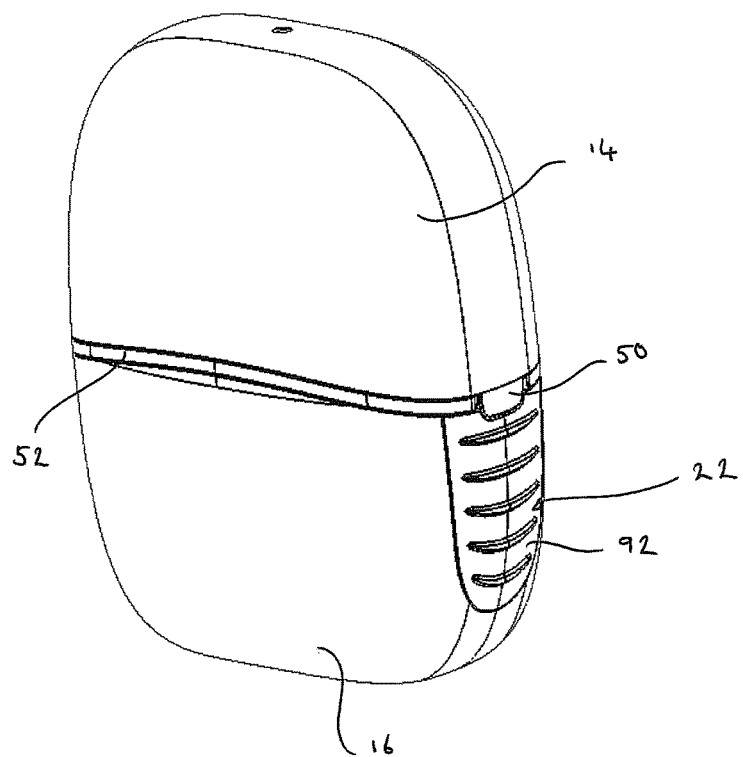
FIG. 12 schematically shows a perspective view of the assembled inhaler with the actuation button in the retracted position.
Figure 13:
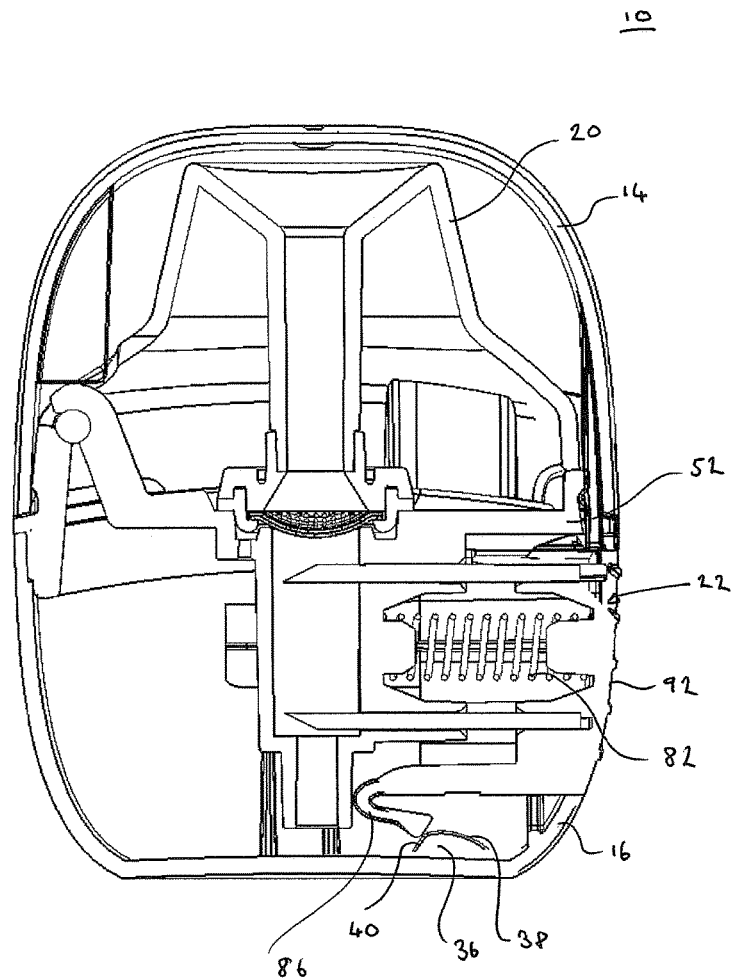
FIG. 13 schematically shows a cross-sectional view of the assembled inhaler with the actuation button in the retracted position.

As shown in FIGS. 12 and 13, in the fully assembled and closed configuration of the inhaler 10 the dispensing assembly 18 is detachably attached to the lower shell part 16 with the retaining projections 30 of the lower shell part 16 located within the retaining recesses 100 of the platform member 52. With the dispensing assembly 18 attached to the lower shell part 16, the platform member 52 extends across the open top 24 of the lower shell part 16, the medicament chamber 54 is disposed within the lower shell part 16, and the actuation button 22 is located within the button cut-out 26. The guide projections 32 of the lower shell part 16 are located in the corresponding guide slots 98 formed in the sides of the actuation button 22. The upper shell part 14 covers the mouthpiece 20 and is retained in this closed configuration by the engagement of the retention projections 48 formed on the inner surface of the upper shell part 14 and the retention recesses 102 formed in the platform member 52.

In the configuration shown in FIGS. 12 and 13, the actuation button 22 is in a retracted position in which the front surface 92 is substantially flush with the outer surface of the lower shell part 16. This provides a sleek outer appearance to the user. The actuation button 22 is retained in this retracted position by upper shell part 14 which is in the closed configuration. In particular, the latching projection 50 of the upper shell part 14 is located over the latching edge 96 provided by the latching recess 94 formed in the actuation button 22. Therefore, the latch formed by the latching projection 50 and the latching recess/edge 94, 96 is engaged and prevents the coil spring 82 from moving the actuation button 22 towards the projected position in which it projects from the outer surface of the lower shell part 14. In order to keep the actuation button 22 in the retracted position, the latch must provide a latch force $F_L$ that is greater than the force biasing the actuation button 22 to the projected position. The first biasing device formed by the coil spring 82 generates a first spring force $F_1$ on the actuation button 22 that acts in a direction towards the projected position. In order to reduce the latch force $F_L$ that the latch must provide, and so as to reduce any creep of the plastics components, a second biasing device provides a second spring force $F_2$ that acts on the actuation button 22 in a direction towards the retracted position.

As can be seen in FIG. 13, the second biasing device is formed by the cooperation of the spring ramp 36 formed on the bottom of the lower shell part 16 and the resilient spring arm 86 formed on the bottom of the actuation button 22. With the actuation button 22 in the retracted position, the end of the spring arm 86 is in contact with the second ramp surface 40 of the spring ramp 36. Therefore, with the actuation button 22 in the retracted position the second biasing device of the ramp and spring arm 36, 86 generates a spring force $F_2$ on the actuation button 22 that acts in a direction towards the retracted position. The latch force $F_L$ that the latch must provide to retain the actuation button 22 in the retracted position is therefore $F_L = F_1 - F_2$.

Figure 14:
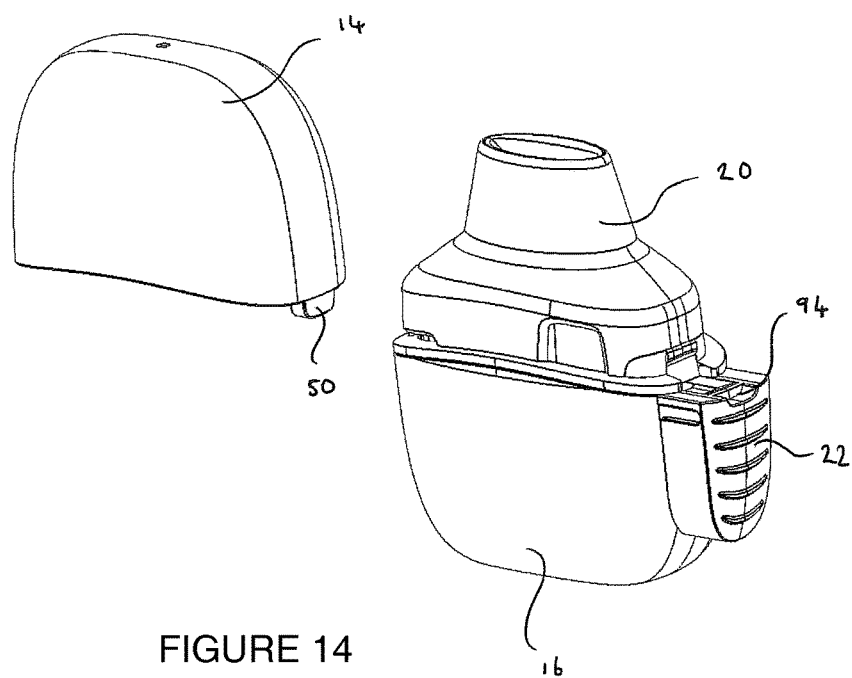
FIG. 14 schematically shows a perspective view of the inhaler with the upper shell part in the open configuration.
Figure 15:
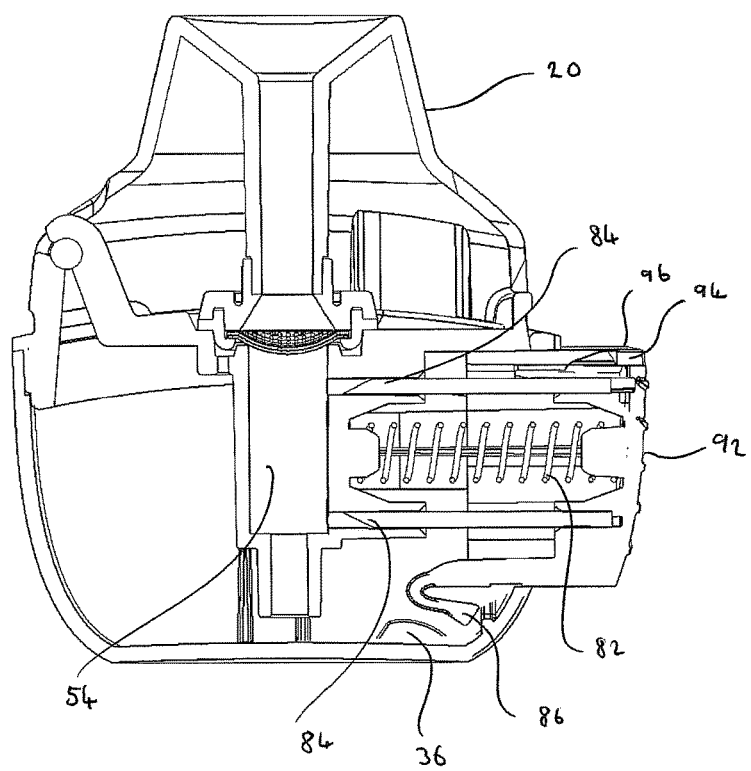
FIG. 15 schematically shows a cross-sectional view of the inhaler with the upper shell part removed.

With reference to FIGS. 14 and 15, in order to use the inhaler 10, the user must remove the upper shell part 14 and move it to an open configuration in which the mouthpiece 20 is exposed. In the open configuration, the upper shell part 14 is completely separated from the lower shell part 16. In order to remove the upper shell part 14, the user must apply some force so as to disengage the retentions projections 48 and the retention recesses 102. When the upper shell part 14 is removed, the latch is disengaged as the latching projection 50 is removed from the latching recess 94. Since the latch no longer provides a latch force and the first spring force $F_1$ generated by the coil spring 82 is greater than the second spring force $F_2$ generated by the ramp/spring arm 36, 86, the actuation button 22 moves towards the projected position shown in FIGS. 14 and 15. During the initial movement of the actuation button 22 away from the retracted position towards the projected position, the end of the spring arm 86 moves over the second inclined ramp surface 40 of the spring ramp 36 and therefore the initial movement of the actuation button 22 is dampened. This prevents the actuation button 22 from moving too rapidly which may be undesirable. As can be seen in FIG. 14, with the actuation button 22 in the projected position it projects from the outer surface of the lower shell part 16. As shown in FIG. 15, with the actuation button 22 in the projected position, the end of the spring arm 86 is not in contact with the spring ramp 36 and therefore the second biasing device does not apply any force on the actuation button 22. Further, after the actuation button 22 has moved to the projected position, the piercing elements 84 are positioned outside of the medicament chamber 54.

Figure 16:
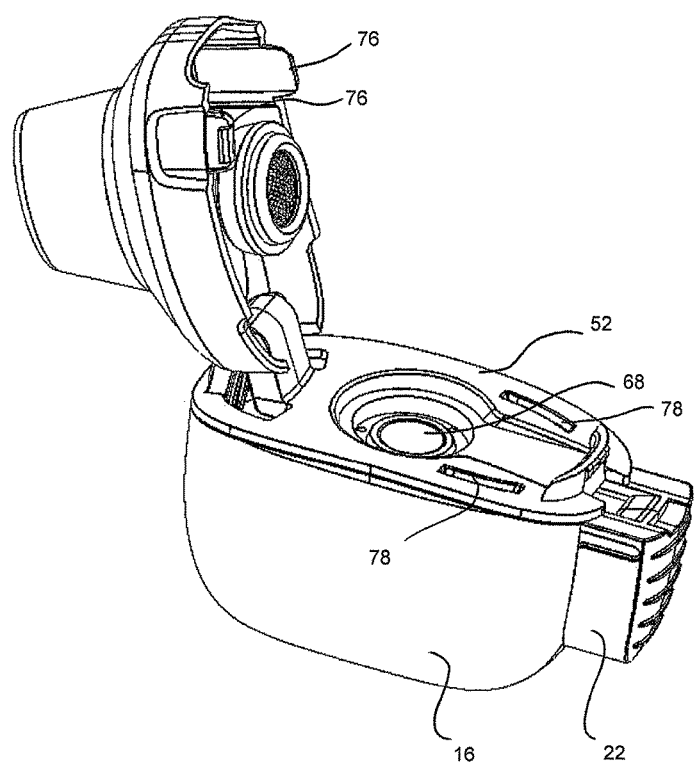
FIG. 16 schematically shows a perspective view of the inhaler with the mouthpiece in the loading position.
Figure 17:
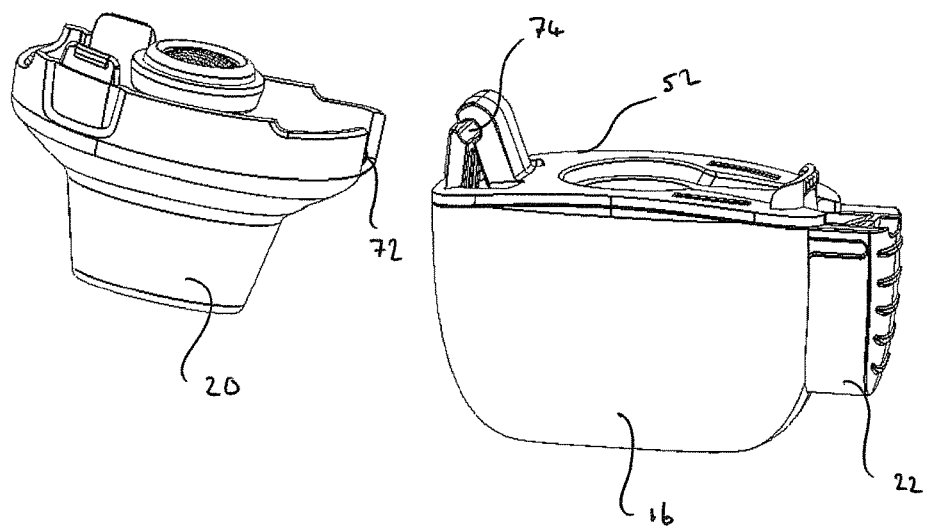
FIG. 17 schematically shows a perspective view of the inhaler with the mouthpiece detached.

After removing the upper shell part 14 and automatically causing the actuation button 22 to move to the projected position the user must load a capsule of dry powder medicament into the medicament chamber 54. With reference to FIG. 16, this is done by pinching the grips 80 provided either side of the mouthpiece 20 which disengages the coupling projections 76 formed on the mouthpiece 20 from the coupling recesses 78 formed in the platform member 52, and pivoting the mouthpiece 20 from the inhaling position (FIG. 14), to the loading position (FIG. 16). In the loading position, the medicament chamber outlet 68 is exposed and a medicament capsule can be loaded into the medicament chamber 54. After a capsule has been loaded into the medicament chamber 54, the mouthpiece 20 is pivoted back to the inhaling position (FIG. 14) and the coupling projections and recesses 76, 78 are engaged to restrict the movement of the mouthpiece. Referring to if the FIG. 17, mouthpiece 20 is over pivoted, the hinge 70 separates as the rod 72 detaches from the slotted opening 74 without damaging either component. This means that if a user accidentally applies too much force, the mouthpiece 20 and platform member 52 separate before structurally damaging either component.

Figure 18:
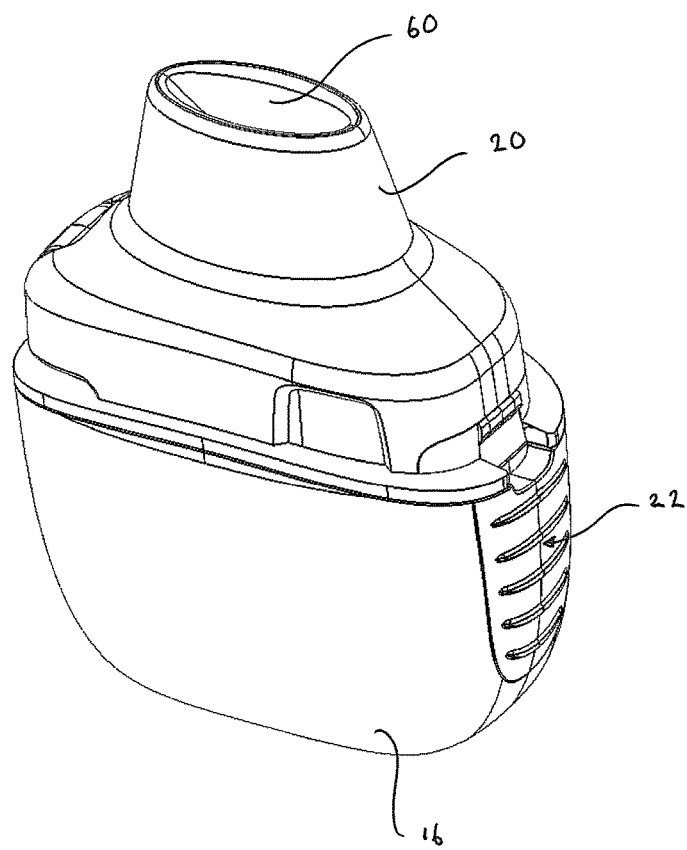
FIG. 18 schematically shows a perspective view of the inhaler with the upper shell part removed and the actuation button in the retracted position.
Figure 19:
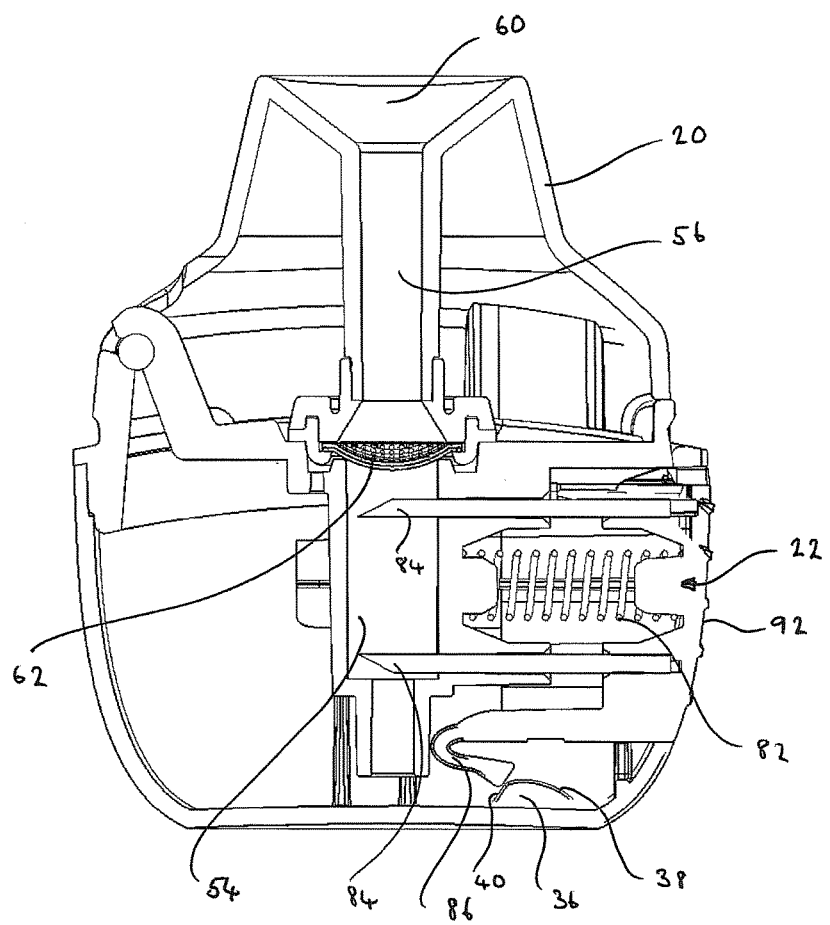
FIG. 19 schematically shows a cross-sectional view of the inhaler with the upper shell part removed and the actuation button in the retracted position.

Once a capsule has been loaded into the medicament chamber 54 and the mouthpiece 20 returned to the inhaling position (FIG. 14), the user depresses the actuation button 22 and moves it towards the retracted position as shown in FIGS. 18 and 19. As the actuation button 22 is moved to the retracted position, the piercing elements 84 enter the medicament chamber 54 and pierce the dry powder medicament capsule located within the medicament chamber 54. This causes the dry powder to be released from the capsule. The user then inhales through the mouthpiece 20 causing the dry powder to be sucked through the medicament chamber 54, past the filter 62, through the inhalation passageway 56 and out of the mouthpiece outlet 60 into the user's respiratory tract. The filter 62 ensures that any capsule debris is retained within the medicament chamber 54 and is not inhaled.

During movement of the actuation button 22 from the projected position to the retracted position, the end of the spring arm 86 rides over the first ramp surface 38 of the spring ramp 36. This generates a second spring force $F_2$ on the actuation button 22 in a direction towards the projected position and therefore the force required to move the actuation button 22 is the sum of the first biasing force $F_1$ generated by the coil spring 82 and the second biasing force $F_2$. However, since the gradient of the first ramp surface 38 is not constant, the second spring force $F_2$ varies depending on the position of the actuation button 22. This provides enhanced tactile or haptic feedback to the user. Once the end of the spring arm 86 rides over the peak region 40 of the ramp 36, the direction of application of the second spring force $F_2$ changes so that it applies a force to the actuation button 22 in a direction towards the retraced position.

As the actuation button 22 is pushed towards the retracted position the guide projections 32 slide within the guide slots 98 of the actuation button 22. However, since the projections 32 are located within and engaged with the slots 98, the complete dispensing assembly 18 is restricted from being removed from the lower shell part 16. This prevents a user from inadvertently causing the dispensing assembly to be detached from the lower shell part 16 as the actuation button 22 is depressed.

After use, the upper shell part 14 can be re-coupled to the lower shell part 16 such that it covers the mouthpiece 20 and is in the closed configuration. The upper shell part 14 can either be replaced with the actuation button 22 in the retracted position, or with the actuation button 22 in the projected position. In either case, due to the orienting latching projection 50, the upper shell part 14 can only be reattached in a single correct orientation. If the upper shell part 14 is reattached with the actuation button 22 in the retracted position, the latching projection 50 simply locates over the latching edge 96 within the latching recess (FIG. 12). This engages the latch and retains the actuation button 22 in the retracted configuration.

Figure 20:
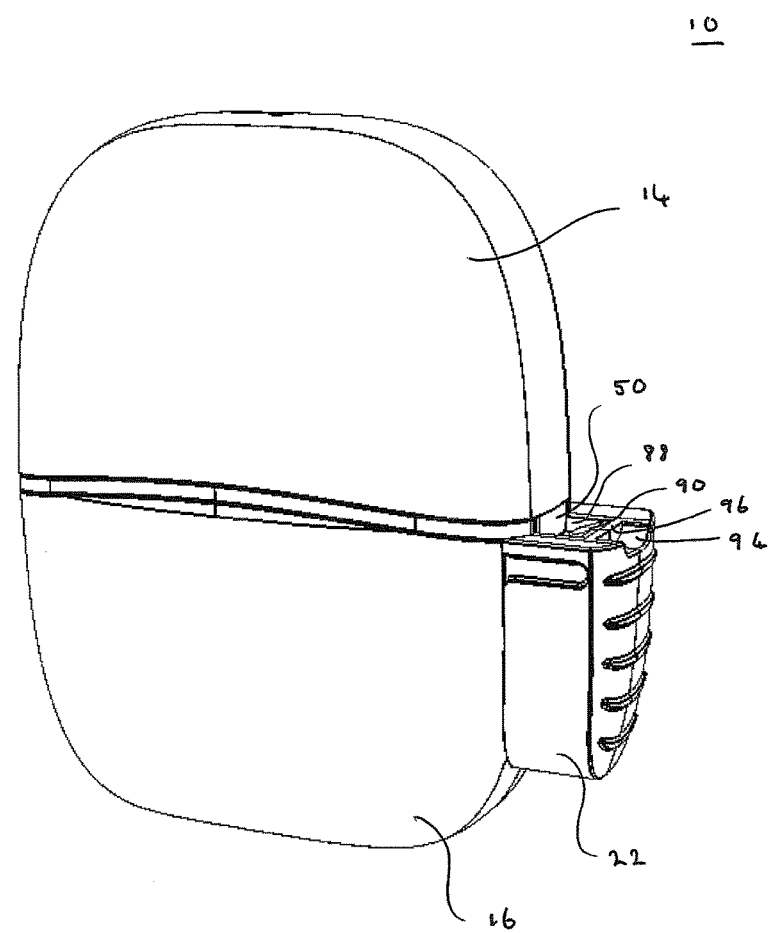
FIG. 20 schematically shows a perspective view of the inhaler with the upper shell part in the closed configuration and the actuation button in the projected position.
Figure 21:
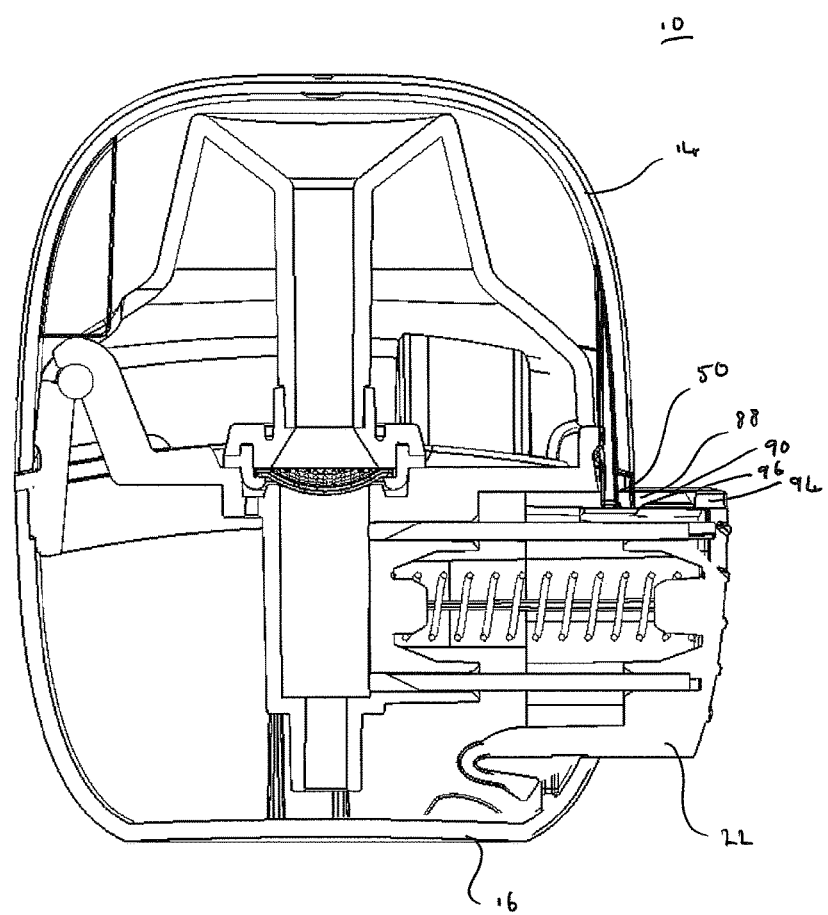
FIG. 21 schematically shows a cross-sectional view of the inhaler with the upper shell part in the closed configuration and the actuation button in the projected position.

As shown in FIGS. 20 and 21, if the upper shell part 14 is reattached with the actuation button 22 in the projected position, the latching projection 50 of the upper shell part 14 locates within the channel 88 formed in the upper surface of the actuation button 22 in front of the ramp 90. If the actuation button 22 is now moved towards the retracted position, the latching projection 50 rides over the ramp 90 formed within the channel 88 which causes the upper shell part 14 to resiliently move slightly away from the closed configuration. As the actuation button 22 is moved further, the latching projection 50 rides over the latching edge 96 and locates within the latching recess 94 thereby engaging the latch (FIGS. 12 and 13). As the latching projection 50 locates within the latching recess 94, the upper shell part 14 moves back to the closed configuration. The engagement of the latch retains the actuation button 22 in the retracted, or stowed, position in which the surface of the actuation button 92 is substantially flush with the outer surface of the lower shell part 16.

Although it has been described that the medicament chamber is a capsule chamber for receiving a sealed dose in the form of a capsule, it should be appreciated it is equally applicable to other types of inhaler. For example, the sealed dose could be a blister provided on a strip or card. Of course, other types of sealed dose could be used and essentially any type of powdered reservoir could be suitable. As opposed to piercing a sealed dose, such as a capsule, to release medicament a sealed dose could be crushed, opened, severed or split, for example. If the sealed dose is a blister, dispensing the medicament could include peeling a foil layer away so as to release the medicament.

The invention claimed is:

1. A dry powder inhaler, comprising:
   a shell comprising an upper shell part and a lower shell part;
   an inhalation piece through which a user can inhale medicament, wherein the inhalation piece is coupled to the lower shell part and wherein the upper shell part is moveable between a closed configuration in which it is coupled to the lower shell part and covers the inhalation piece, and an open configuration in which the inhalation piece is exposed;
   an actuation button coupled to the lower shell part and biased by a first biasing device located and acting between the actuation button and the lower shell part towards a projected position in which it projects from the surface of the lower shell part and moveable to a retracted position; wherein in use, movement of the actuation button from the projected position towards the retracted position causes medicament to be dispensed for subsequent inhalation through the inhalation piece; and
   a latch which when engaged retains the actuation button in the retracted position.

2. The inhaler of claim 1, wherein the latch comprises a latching projection that is configured to be located over a corresponding latching edge so as to engage the latch.

3. The inhaler of claim 2, wherein the upper shell part comprises the latching projection or the latching edge, and the actuation button comprises the other of the latching projection or latching edge.

4. The inhaler of claim 3, wherein when the actuation button is in the retracted position and the upper shell part is in the closed configuration, the latching projection is located over the latching edge so as to engage the latch and retain the actuation button in the retracted position.

5. The inhaler of claim 4, wherein with the upper shell part in the closed configuration, movement of the actuation button from the projected position to the retracted position causes the latching projection to locate over the latching edge and the latch to be engaged.

6. The inhaler of claim 2, wherein the latching edge is the edge of a latching recess within which the latching projection is located when located over the latching edge.

7. The inhaler of claim 4, wherein the upper shell part comprises the latching projection and the actuation button comprises the latching edge and a ramp which is inclined and terminates towards the latching edge, wherein with the upper shell part in the closed configuration, movement of the actuation button from the projected position to the retracted position causes the latching projection to ride over the ramp allowing the latching projection to locate over the latching edge and the upper shell part to return to the closed configuration, thereby engaging the latch.

8. The inhaler of claim 1, wherein regardless of the position of the actuation button, the first biasing device applies a first spring force to the actuation button which acts in a direction towards the projected position.

9. The inhaler of claim 8, further comprising a second biasing device that is configured to act between the actuation button and the lower shell part, wherein depending on the position of the actuation button, the second biasing device applies a second spring force to the actuation button, the magnitude and the direction of action of which depends on the position of the actuation button.

10. The inhaler of claim 9, wherein the second biasing device comprises a ramp and a corresponding spring arm, the relative positions of which vary with the position of the actuation button, wherein the magnitude and the direction of action of the second spring force depends on the relative positions of the ramp and spring arm.

11. The inhaler of claim 10, wherein the lower shell part comprises the ramp or spring arm, and the actuation button comprises the other of the ramp or spring arm.

12. The inhaler of claim 11, further comprising a medicament chamber in fluid communication with the inhalation piece and arranged to receive medicament, wherein in use, movement of the actuation button from the projected position towards the retracted position causes the medicament to be dispensed so that the medicament can subsequently be inhaled through the inhalation piece.

13. The inhaler of claim 12, further comprising a piercing or opening element arranged such that in use movement of the actuation button from the projected position towards the retracted position causes a sealed dose located within the medicament chamber to be pierced or opened, thereby dispensing the medicament.

14. The inhaler of claim 10, wherein the ramp has first and second ramp surface portions inclined in generally opposing directions and which converge at a peak region.

15. The inhaler of claim 9, wherein as the actuation button is moved towards the retracted position, the second spring force acts in a direction towards the projected position.

16. The inhaler of claim 9, wherein when the actuation button is in the retracted position, the second spring force acts in a direction towards the retracted position.

17. The inhaler of claim 9, wherein when the actuation button is in the projected position the second biasing device does not act on the actuation button.

18. The inhaler of claim 9, wherein during initial movement of the actuation button from the retracted position towards the projected position caused by the first biasing device, the second spring force acts in a direction towards the retracted position so as to dampen the initial movement of the actuation button.

19. The inhaler of claim 1, wherein in the retracted position, the actuation button is substantially flush with the lower shell part.

20. The inhaler of claim 1, wherein the upper shell part is completely separable from the lower shell part.

* * * * *